United States Patent
Teschner et al.

(10) Patent No.: US 8,105,242 B2
(45) Date of Patent: Jan. 31, 2012

(54) PROCESS AND DEVICE FOR LUNG VENTILATION

(75) Inventors: Eckhard Teschner, Luebeck (DE); Dieter Weismann, Gross Groenau (DE)

(73) Assignee: Dräger Medical GmbH, Lübeck (DE)

( * ) Notice: Subject to any disclaimer, the term of this patent is extended or adjusted under 35 U.S.C. 154(b) by 1181 days.

(21) Appl. No.: 11/675,872

(22) Filed: Feb. 16, 2007

(65) Prior Publication Data

US 2007/0246047 A1 Oct. 25, 2007

(30) Foreign Application Priority Data

Apr. 19, 2006 (DE) .................. 10 2006 018 199

(51) Int. Cl.
*A61B 5/08* (2006.01)
(52) U.S. Cl. ........................................ 600/529; 600/547
(58) Field of Classification Search .................. 600/533, 600/529
See application file for complete search history.

(56) References Cited

U.S. PATENT DOCUMENTS

| | | | |
|---|---|---|---|
| 5,660,170 A * | 8/1997 | Rajan et al. .............. | 128/204.18 |
| 2003/0095692 A1* | 5/2003 | Mundy et al. ................ | 382/128 |
| 2003/0216664 A1* | 11/2003 | Suarez ......................... | 600/547 |

FOREIGN PATENT DOCUMENTS

| | | | |
|---|---|---|---|
| DE | 198 57 090 A1 | 6/2000 |
| EP | 0 745 402 A1 | 12/1996 |
| EP | 1 137 365 B1 | 10/2001 |
| EP | 1137365 B1 * | 7/2005 |

* cited by examiner

*Primary Examiner* — Miranda Le
*Assistant Examiner* — Michael R Bloch
(74) *Attorney, Agent, or Firm* — McGlew and Tuttle, P.C.

(57) ABSTRACT

A process with a corresponding device for lung ventilation involves recording an image of the lung status with an electric impedance tomography (EIT) system (2) and the total area of ventilated lung areas is determined by a computing unit (4) from all image values, subsequently divided into at least two lung areas and the extent of the homogeneity of the ventilated lung areas is determined by comparison of the impedance changes within these areas. In case of a homogeneity rated as being too low, the respiration pressures are increased step by step by means of the respirator (1) and the respiration pressure at which the greatest possible homogeneity is obtained from subsequently determined status images is determined by means of the EIT system (2). The respiration pressure is subsequently lowered again by the respirator (1) until the computing unit (4) detects a reduction in the homogeneity of ventilated lung areas, so that the respiration pressure is subsequently increased again by means of the respirator (1) to the last value at which no reduction in the homogeneity of the ventilated lung areas occurred.

20 Claims, 1 Drawing Sheet

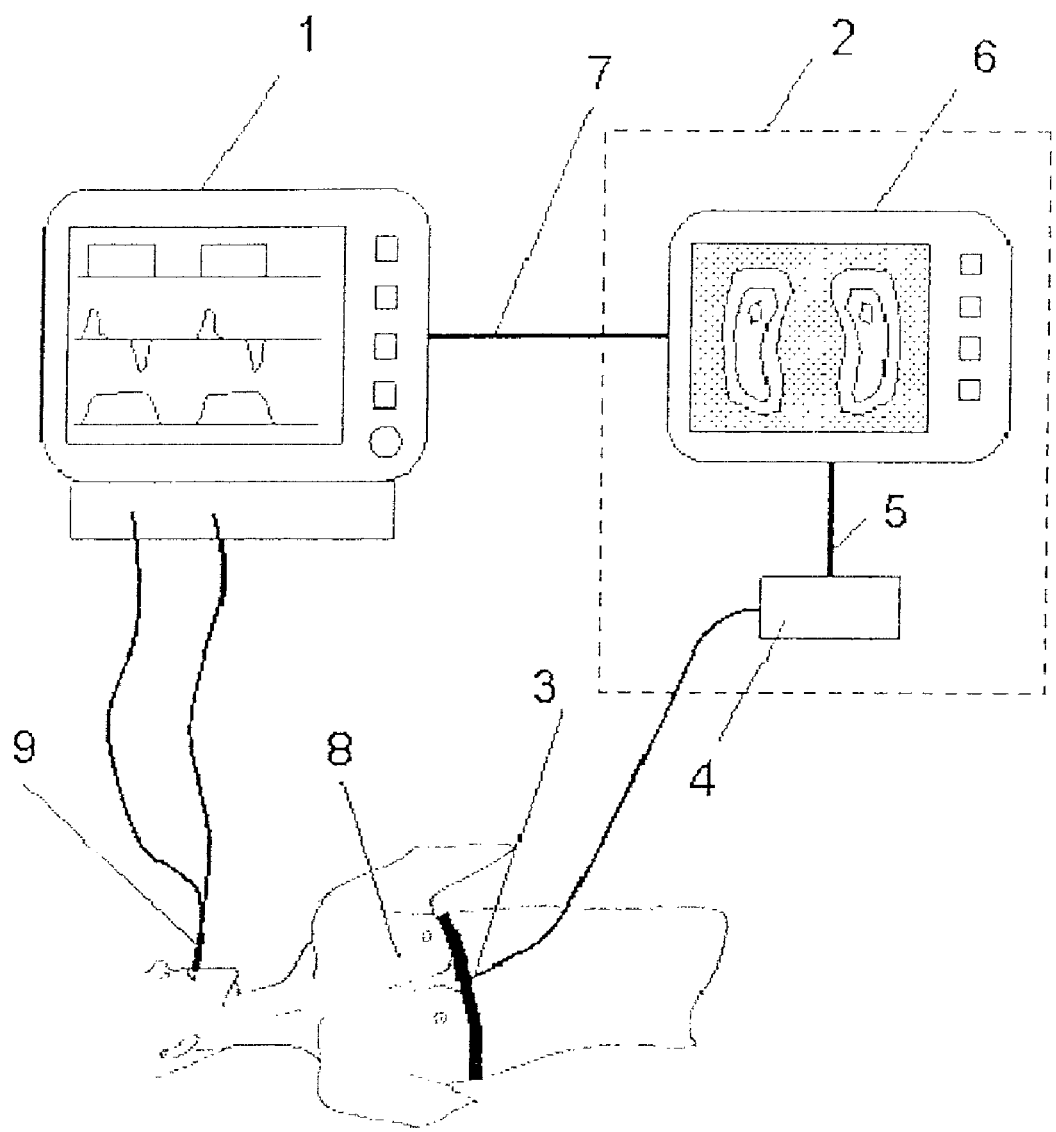

PROCESS AND DEVICE FOR LUNG VENTILATION

CROSS REFERENCE TO RELATED APPLICATIONS

This application claims the benefit of priority under 35 U.S.C. §119 of German Patent Application DE 10 2006 018 199.9 filed Apr. 19, 2006, the entire contents of which are incorporated herein by reference.

FIELD OF THE INVENTION

The present invention pertains to a process and a device for lung ventilation (also known as lung respiration).

BACKGROUND OF THE INVENTION

Electric impedance tomography (EIT) is a process, which is known per se, in which the electric impedance between the feed point and the test point can be calculated by feeding an alternating electric current of, e.g., 5 mA$_{eff}$ at 50 kHz into any electrically conductive body, here preferably into the human body, and measuring the surface potentials resulting therefrom at different points of the body. A two-dimensional tomogram of the electric impedance distribution in the body being considered can be determined on the basis of suitable mathematical reconstruction algorithms by gradually rotating the current feed sites around the body while measuring at the same time the surface potentials along a section plane.

Such a tomogram of the impedance distribution of the human body is of interest in medicine because the electric impedance changes both with the air content and the extracellular fluid content in the tissue. It is thus possible to visualize and monitor with this process especially the ventilation, i.e., the ventilation of the lungs, as well as the changes in the end-expiratory lung volume in a regionally resolved manner.

It is known that ventilated lung areas as well as the changes therein over time can be represented by means of EIT.

For example, the clinical advantages that arise from the reopening of previously closed lung areas are described in detail in the patent "METHODS AND APPARATUS FOR DETERMINING ALVEOLAR OPENING AND CLOSING," EP 1 137 365 B1. However, this known patent is based on the assumption that the opening and closing of alveoli can be determined by means of EIT and respiration pressures can then be set on the basis of these findings such that the alveoli will just remain open at the end of the expiration.

However, there typically are very great inhomogeneities in terms of ventilation in the thoracic cross section plane in intensive care patients with severe lung diseases, in whom alveolar closing is to be suspected, so that it cannot be assumed that all alveoli behave in the same manner in the EIT voxel ("volume pixel") being considered. Thus, it appears to be more than questionable whether impedance values that are correlated with the alveolar closing and opening to an acceptable extent can be determined with the prior-art process proposed. It would even be possible in the extreme case in boundary areas between open lung areas and lung areas that cannot be opened based on the EIT voxel size that already opened lung areas are over-distended and this over-distension would be misinterpreted as opening of closed lung areas because of the increase in impedance changes that results herefrom.

SUMMARY OF THE INVENTION

The object of the present invention is therefore to propose an improved process and a device for operating a respirator connected to an EIT system for gentle lung ventilation, taking into account the limited spatial resolution of EIT.

According to the invention, a process is provided for lung ventilation. The process includes providing a combination of an electric impedance tomography system, a computing unit and a respirator. A first image of the pulmonary status is recorded with the electric impedance tomography system. A total area of the ventilated lung area is determined from all image values by the computing unit and this total area is subsequently divided into at least two lung ventilated lung areas and determining an extent of homogeneity of the ventilated lung areas by comparison of the impedance changes within these areas. The respiration pressure is increased step by step, with the respirator, in case of a homogeneity rated as being too low and the respiration pressure at which the greatest possible homogeneity of the ventilated lung areas is obtained from the status images determined subsequently is determined by means of the electric impedance tomography system. The respiration pressure is subsequently lowered step by step with the respirator, until the computing unit detects a reduction of the homogeneity of the ventilated lung areas, and subsequently again the respiration pressure is increased step by step with the respirator to the last value at which no reduction of the homogeneity of the ventilated lung areas occurred.

The determination of the homogeneity may be based on the time curve of the inspiratory impedance changes, which is concave especially in areas of low compliance and convex in areas of high compliance as a consequence of over-distension. The determination of the homogeneity may be carried out at the time of the simultaneous beginning of inspiration in the individual lung areas. The homogeneity may be determined from the ratio of local impedance changes over time to global impedance, pressure or volume changes over time. The homogeneity may be determined from the comparison of the spatial distribution of the impedance changes within the individual lung areas.

An expert system may be stored in the computing unit. Based on this, the electric impedance tomography system indicates the changes in the current respiration settings on the respirator that lead to more homogeneous ventilation of the lungs.

The stepwise increase in the respiration pressure may advantageously be carried out in a continuously decreasing manner.

After a comparison of the homogeneity values and after a comparison with reference values stored in the computing unit, termination signals may be sent to the respirator for the stepwise increase in the respiration pressures.

A calibration may be carried out with absolute impedance measurements to compensate a water content changing over time in the lungs.

According to another aspect of the invention, a device for lung ventilation is provided, with the device comprising an electric impedance tomography system, a computing unit and a respirator. The electric impedance tomography system records an image of the lung status and determines the total area of ventilated lung areas from all image values by means of the computing unit. The computing unit subsequently divides this total area into at least two lung areas and determines an extent of homogeneity of the ventilated lung areas by comparison of the impedance changes within these areas. The respirator increases respiration pressures step by step in case of a homogeneity rated as being too low and determines with the electric impedance tomography system a respiration pressure at which a greatest possible homogeneity of the ventilated lung areas is obtained from the subsequently determined status images. The respirator subsequently reduces the respiration pressure step by step until the computing unit detects a reduction in the homogeneity of the ventilated lung areas. The respirator again increases the respiration pressure to the last value at which no reduction in the homogeneity of the ventilated lung areas occurred.

An exemplary embodiment of the present invention will be explained below on the basis of the only FIGURE. The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which preferred embodiments of the invention are illustrated.

BRIEF DESCRIPTION OF THE DRAWING

In the drawing:

The only FIGURE is a schematic view showing the principal components of a device for carrying out the process.

DESCRIPTION OF THE PREFERRED EMBODIMENTS

Referring to the drawing in particular, according to the invention, the EIT system 2 contains an evaluating and display unit 6 and detects a first image of the lung status of a patient 8.

The EIT system 2 is equipped with a computing unit 4, which defines all image values, whose impedance changes within a certain frequency range exceeding a certain threshold value, as ventilated lung areas and thus determines a value that represents the total area of the ventilated lung areas. The computing unit 4 may also be arranged separately outside the EIT system 2, for example, between the evaluating and display unit 6 and the respirator 1. Furthermore, it would be technically conceivable that the EIT system 2 is arranged in an integrated total system together with the computing unit 4 and the respirator 1. The computing unit 4 is connected to the evaluating and display unit 6 via the line 5. The computing unit 4 is connected to the patient 8 via the line 3.

In addition, the computing unit 4 determines the spatial distribution of ventilation within a number of regions of interest (ROI) and calculates how uniformly the lung areas, which are represented by the individual ROIs, are ventilated.

The information determined by the computing unit 4 is sent to the respirator 1 connected via a bidirectional data connection 7. The patient 8 is respirated via a patient connection piece 9 via the respirator 1.

While additional images of the pulmonary status are continuously generated, the respirator 1 gradually increases the respiration pressures and the tidal volumes and continuously compares the first status image with the particular current status images that may possibly change as a consequence of the increase in the respiration pressures.

The increase in the respiration pressure and the tidal volumes is stopped as soon as the total area of the current status image no longer changes.

The respiration pressures are subsequently lowered step by step to the extent that the computing unit recognizes a decrease in the ventilated lung areas, and the respirator 1 again increases the respiration pressures to the last value at which no differences were still determined or, as an alternative, until the greatest possible homogeneity was reached between the ROIs being considered. As an alternative, the respirator 1 applies respiration volumes that are associated with corresponding respiration pressures.

While specific embodiments of the invention have been shown and described in detail to illustrate the application of the principles of the invention, it will be understood that the invention may be embodied otherwise without departing from such principles.

What is claimed is:

1. A process for lung ventilation, the process comprising:
providing a combination of an electric impedance tomography system, a computing unit and a respirator;
recording a first image of pulmonary status with the electric impedance tomography system;
determining a value of total area of a ventilated lung area by the computing unit from all image values, whose impedance changes exceed a predetermined value within a predetermined frequency range, and subsequently dividing the total area into at least two ventilated lung areas and determining an extent of ventilation homogeneity of the at least two ventilated lung areas by comparison of the impedance changes within these areas;
increasing respiration pressure step by step, with the respirator, in case of a ventilation homogeneity rated as being too low;
further recording a plurality of status images with said electric impedance tomograph system after said respiration pressure is increased;
determining a respiration pressure at which a greatest possible ventilation homogeneity of the at least two ventilated lung areas occurs based on the total area values of said plurality of status images by means of the electric impedance tomography system; and
lowering the respiration pressure step by step with the respirator, subsequent to said increasing respiration pressures step by step, until the computing unit detects a reduction of the ventilation homogeneity of the at least two ventilated lung areas, and subsequently again increasing the respiration pressure step by step with the respirator to a last value of the ventilated lung area at which no reduction of the ventilation homogeneity of the at least two ventilated lung areas occurred.

2. A process in accordance with claim 1, wherein the determination of the ventilation homogeneity is based on a time curve of the impedance changes, which is concave especially in areas of low compliance and convex in areas of high compliance as a consequence of over-distension.

3. A process in accordance with claim 1, wherein the determination of the ventilation homogeneity is carried out at a time of a simultaneous beginning of inspiration in the at least two ventilated lung areas.

4. A process in accordance with claim 1, wherein the ventilation homogeneity is determined from a ratio of local impedance changes over time to global impedance, pressure or volume changes over time.

5. A process in accordance with claim 1, wherein the ventilation homogeneity is determined from a comparison of a spatial distribution of the impedance changes within a first of the at least two ventilated lung areas.

6. A process in accordance with claim 1, wherein based on an expert system stored in the computing unit, the electric impedance tomography system indicates changes in current respiration settings on the respirator that lead to more homogeneous ventilation of the lung areas.

7. A process in accordance with claim 1, wherein the step-by-step increase in the respiration pressure is carried out in a continuously decreasing manner.

8. A process in accordance with claim 1, further comprising:
comparing ventilation homogeneity values and reference values, wherein after comparing homogeneity values and after comparing with reference values stored in the computing unit, termination signals are sent to the respirator for the step-by-step increase in the respiration pressures.

9. A process in accordance with claim 1, wherein calibration is carried out with absolute impedance measurements to compensate a water content changing over time in the lungs.

10. A device for lung ventilation, the device comprising: an electric impedance tomography system; a computing unit; and a respirator, said electric impedance tomography system recording an image of the lung status and determining a value of a total area of ventilated lung areas by means of the computing unit, said computing unit subsequently dividing said total area into at least two lung areas and determining an extent of ventilation homogeneity of the ventilated lung areas by comparison of impedance changes within said at least two lung areas, said respirator increasing respiration pressures step by step in case of a ventilation homogeneity rated as being too low and determining via the ventilated lung area values a respiration pressure at which a greatest possible ventilation homogeneity of the at least two ventilated lung areas is obtained from the subsequently determined status images, and said respirator subsequently reducing the respiration pressure step by step until the computing unit detects a reduction in the ventilation homogeneity of the at least two ventilated lung area values, and the respirator again increasing the respiration pressure to a last value of the ventilated lung area at which no reduction in the ventilation homogeneity of the at least two ventilated lung areas occurred.

11. A device in accordance with claim 10, wherein said computing unit makes a determination of ventilation homogeneity based on a time curve of the impedance changes, which is concave especially in areas of low compliance and convex in areas of high compliance as a consequence of over-distension.

12. A device in accordance with claim 10, wherein said computing unit makes a determination of ventilation homogeneity at a time of a simultaneous beginning of inspiration in the at least two ventilated lung areas.

13. A device in accordance with claim 10, wherein said computing unit makes a determination of ventilation homogeneity from a ratio of local impedance changes over time to global impedance, pressure or volume changes over time.

14. A device in accordance with claim 10, wherein said computing unit makes a determination of ventilation homogeneity from a comparison of the spatial distribution of the impedance changes within a first of the at least two ventilated lung areas.

15. A device in accordance with claim 10, wherein based on an expert system stored in the computing unit, the electric impedance tomography system indicates the changes in the current respiration settings on the respirator that lead to more homogeneous ventilation of the lung areas.

16. A device in accordance with claim 10, wherein said respirator provides said step-by-step increase in the respiration pressure in a continuously decreasing manner.

17. A device in accordance with claim 10, wherein said computing unit compares ventilation homogeneity values and reference values, wherein after comparison of the ventilation homogeneity values and after comparison with reference values are stored in the computing unit, said computing unit sends termination signals to the respirator for the step-by-step increase in the respiration pressures.

18. A device in accordance with claim 10, wherein calibration is carried out with absolute impedance measurements to compensate a water content changing over time in the lungs.

19. A process for lung ventilation, the process comprising:
providing an electric impedance tomography system;
providing a computing unit;
providing a respirator;
recording a first image of pulmonary status with the electric impedance tomography system;
determining a value of a total area of a ventilated lung area based on image values of said first image of pulmonary status via said computing unit;
dividing said total area of said ventilated lung area into at least two ventilated lung areas;
detecting impedance changes within said at least two ventilated lung areas with said electric impedance tomography system, said impedance changes within one of said at least two ventilated lung areas corresponding to a first ventilation homogeneity value, said impedance changes within another one of said at least two ventilated lung areas corresponding to a second ventilation homogeneity value;
comparing said first ventilation homogeneity value with said second ventilation homogeneity value to define a comparison of ventilation homogeneity values;
determining a ventilation homogeneity rating of said at least two ventilated lung areas based on said comparison of ventilation homogeneity values, said ventilation homogeneity rating corresponding to a degree of uniform ventilation of said at least two ventilated lung areas;
increasing a respiration pressure step by step, with said respirator, when said ventilation homogeneity rating is less than a predetermined ventilation homogeneity rating;
further recording a plurality of status images with said electric impedance tomograph system after said respiration pressure is increased;
determining a respiration pressure corresponding to a greatest possible ventilation homogeneity rating of said at least two ventilated lung areas based on said plurality of status images via said electric impedance tomography system;
lowering the respiration pressure step by step with the respirator, subsequent to said increasing respiration pressures step by step, until said computing unit detects a reduction of said ventilation homogeneity rating of said at least two ventilated lung areas; and
increasing the respiration pressure step by step, subsequent to lowering said respiration pressure step by step, with the respirator to a last respiration pressure value at which no reduction of said ventilation homogeneity rating of said at least two ventilated lung areas occurred.

20. A process in accordance with claim 19, wherein the determination of the ventilation homogeneity rating is based on a time curve of inspiratory impedance changes, which is concave in areas of low compliance and convex in areas of high compliance as a consequence of over-distension, at least one total area value being determined for at least one of said plurality of said status images.

* * * * *